United States Patent
Mishima et al.

(10) Patent No.: US 6,932,986 B2
(45) Date of Patent: Aug. 23, 2005

(54) ESSENTIAL OIL MIXTURE FOR MITICIDE, MITICIDE COMPOSITION, AND SPRAY FOR MITICIDE

(75) Inventors: Yasutaka Mishima, Hiratsuka (JP); Hideaki Ohta, Ohta-ku (JP); Akitaka Suetomi, Chuo-ku (JP)

(73) Assignees: Takasago International Corporation, Tokyo (JP); Ube Material Industries, Ltd., Yamaguchi (JP)

( * ) Notice: Subject to any disclaimer, the term of this patent is extended or adjusted under 35 U.S.C. 154(b) by 413 days.

(21) Appl. No.: 10/118,042

(22) Filed: Apr. 9, 2002

(65) Prior Publication Data

US 2002/0176899 A1 Nov. 28, 2002

(30) Foreign Application Priority Data

Apr. 11, 2001 (JP) ..................................... P. 2001-112185

(51) Int. Cl.⁷ ........................ A01N 65/00; A61K 35/78
(52) U.S. Cl. ....................... 424/725; 424/742; 424/745; 424/747
(58) Field of Search ................. 424/742, 747, 424/745, 726, 725

(56) References Cited

U.S. PATENT DOCUMENTS 6,444,238 B1 * 9/2002 Weise ........................ 424/736

2003/0194454 A1 * 10/2003 Bessette et al. ............. 424/745

FOREIGN PATENT DOCUMENTS

| CH | 688 787 A5 | 3/1998 |
| DE | 198 24 683 A1 | 12/1999 |
| EP | 0 737 479 A1 | 10/1996 |
| JP | 5-178712 A | 7/1993 |
| WO | WO 01/01782 A1 | 1/2001 |

OTHER PUBLICATIONS

XP–002205184, Abstract of JP 04–305505 (Oct. 28, 1992).
Patent Abstracts of Japan—2002053415 (Feb. 19, 2002).
Patent Abstracts of Japan—02251669 (Oct. 9, 1990).
XP–002205186, Abstract of JP 2001–031508 (Feb. 6, 2001).
XP–002205185, Abstract of Rachna et al article (1995).
European Search Report dated Aug. 30, 2002.

* cited by examiner

*Primary Examiner*—Kent Bell
(74) *Attorney, Agent, or Firm*—Sughrue Mion, PLLC

(57) ABSTRACT

An essential oil mixture for miticide, which contains eucalyptus oil or rosemary oil or a mixture thereof and a mint oil in amounts within a range of from 1:4 to 1:99 by mass ratio, and a miticide in which the essential oil mixture for miticide is dissolved in a solvent. The miticide composition which hardly gives users unpleasant feeling when applied in an amount by which sufficient miticide effect can be obtained.

9 Claims, No Drawings

ESSENTIAL OIL MIXTURE FOR MITICIDE, MITICIDE COMPOSITION, AND SPRAY FOR MITICIDE

FIELD OF THE INVENTION

This invention relates to a miticide which contains natural essential oil as the active ingredient.

BACKGROUND OF THE INVENTION

It is known that certain aromatic raw materials and natural essential oils and terpene compounds contained therein have mite-repelling effect or miticide effect.

For example, JP-A-5-178712 discloses mite-repelling effect by aromatic raw materials such as benzyl formate, benzyl acetate, benzyl propionate, benzyl butyrate, benzyl valerate, benzyl caproate, benzyl phenyl ketone and benzophenone, terpene compounds such as linalool and limonene, and natural essential oils such as lemongrass oil, geranium oil, rosemary oil, laurel oil, peppermint oil, spearmint oil, lavender oil, caraway oil, cassia oil, calamus oil, fennel oil and thyme oil.

Since natural essential oils are substances having extremely high safety for human bodies, it is desirable if mites can be controlled using natural essential oils. However, according to studies carried out by the present inventors, it was revealed that when a natural essential oil is applied to a habitat of mites in an amount by which high miticide effect can be obtained, the smell of the natural essential oil in its surroundings becomes extremely strong which causes a tendency to give its user and those around the site unpleasant feeling.

SUMMARY OF THE INVENTION

An object of the invention is to provide a miticide which hardly gives unpleasant feeling to users when it is applied in an amount by which sufficient miticide effect can be obtained.

The present invention provides the following invention.

(1) An essential oil mixture for miticide, which comprises eucalyptus oil or rosemary oil or a mixture thereof and a mint oil in amounts within a range of from 1:4 to 1:99 by mass ratio.

(2) The essential oil mixture for miticide according to (1) above, wherein the mint oil is peppermint oil.

(3) A miticide composition which comprises an essential oil mixture for miticide comprising eucalyptus oil or rosemary oil or a mixture thereof and a mint oil in amounts within a range of from 1:4 to 1:99 by mass ratio.

(4) The miticide composition according to (3) above, wherein the mint oil is peppermint oil.

(5) A miticide composition which comprises a solvent and an essential oil mixture for miticide dissolved in said solvent, said essential oil mixture for miticide comprising eucalyptus oil or rosemary oil or a mixture thereof and a mint oil in amounts within a range of from 1:4 to 1:99 by mass ratio.

(6) The miticide composition according to (5) above, wherein a content of the essential oil mixture for miticide is within a range of from 3 to 20% by mass based on the total amount of the miticide composition.

(7) The miticide composition according to (5) above, wherein the mint oil is peppermint oil.

(8) A spray for miticide, which comprises a closed container having a spray nozzle and the miticide composition of any one of (3) to (7) above packed therein.

DETAILED DESCRIPTION OF THE INVENTION

The essential oil mixture for miticide of the invention is characterized in that it contains eucalyptus oil or rosemary oil or a mixture thereof, and a mint oil. That is, it is characterized in that it contains a mint oil which has excellent miticide effect, among natural essential oils, and eucalyptus oil and/or rosemary oil which promote the miticide effect of the mint oil.

A mixing ratio of the eucalyptus oil or rosemary oil or a mixture thereof with the mint oil is within a range of from 1:4 to 1:99 (eucalyptus oil or rosemary oil or a mixture thereof:mint oil) by mass ratio, preferably within a range of from 1:4 to 1:30, more preferably within a range of from 1:5 to 1:25.

A mixing ratio in the case of using eucalyptus oil and rosemary oil may be selected in the appropriate range.

As the mint oil, peppermint oil, a distilled oil (an essential oil obtained by distilling mint), a dementholized oil (an essential oil after precipitation of menthol from the distilled oil), spearmint oil and the like can be used alone or as a mixture of two or more. Among these mint oils, it is desirable to use peppermint oil or spearmint oil, and particularly desirable to use peppermint oil.

The essential oil mixture for miticide of the invention may contain a natural essential oil other than the above natural essential oils and a terpene compound.

Examples of the natural essential oil include almond bitter oil, caraway oil, ho oil, bay oil, clove oil, cassia oil, ylang-ylang oil, geranium oil, fennel oil, sage oil, perilla oil, bois de rose oil and the like.

Examples of the terpene compound include linalool, anethole, carvone, benzaldehyde, benzyl alcohol, eugenol, dihydromyrcenol, cineol, camphor, methyl anthranilate, geraniol, limonene, thymol, paraisopropylanisole, citral, borneol and the like.

When the essential oil mixture for miticide of the invention is applied to a habitat of mites, it is desirable to apply it by dissolving in a solvent.

As the solvent, one or more of alcohols such as ethyl alcohol, isopropyl alcohol, ethylene glycol, glycerol, propylene glycol, dipropylene glycol and 1,3-butylene glycol, or a mixed solution of these solvents with water, can be used.

The content of the essential oil mixture for miticide of the invention to be contained in the solvent is generally within a range of from 3 to 20% by mass, preferably within a range of from 5 to 20% by mass, more preferably within a range of from 9 to 12% by mass (based on the total amount of the composition).

The solvent containing the essential oil mixture for miticide of the invention, that is, miticide composition is generally used by packing in a closed container having a spray nozzle such as spray can. Known gas such as methyl fluoride, isobutane, carbon dioxide, liquefied petroleum gas or dimethyl ether can be used as the propellant.

EXAMPLE 1

The miticide effect was evaluated on the following essential oil solutions (A) to (C).

(1) Essential Oil Solution (A)

An essential oil mixture was obtained by mixing eucalyptus oil and peppermint oil at a weight ratio of 1:5. Next, 12 parts by mass of this essential oil mixture was mixed with 88 parts by mass of 95% by volume ethanol aqueous solution to obtain the essential oil solution (A).

(2) Essential Oil Solution (B)

An essential oil mixture was obtained by mixing rosemary oil and peppermint oil at a weight ratio of 1:5. Next, 12 parts by mass of this essential oil mixture was mixed with 88 parts by mass of 95% by volume ethanol aqueous solution to obtain the essential oil solution (B).

(3) Essential Oil Solution (C)

An essential oil solution (C) was obtained by mixing 13 parts by mass of peppermint oil with 87 parts by mass of 95% by volume ethanol aqueous solution.

Evaluation Method of Miticide Effect

A total of 50 individuals of the mite to be tested (belonging to *Dermatophagoides*: female) were allowed to crawl on a 10 cm×10 cm filter paper (mfd. by Advantech, No. 5C). Each of the essential oil solutions was sprayed on the filter surface side where the mite individuals to be tested were allowed to crawl. Immediately after the spraying, weight of the filter paper was weighed and the increased weight was used as the sprayed amount of the essential oil solution. Next, the filter paper was folded in two, and the opening three sides were fastened with eye clips. After 30 minutes or 24 hours of the spraying of the essential oil solution, the filter paper was opened to count the number of resting mite individuals (knocked down numbers).

After counting knocked down numbers after 24 hours, the resting mite individuals were transferred onto another filter paper free from the essential oil solution. Thereafter, knocked down numbers after 24 hours of resting (the number of mite individuals still under resting state) were counted to be used as the number of deaths. During the testing period, the temperature in the test room was from 23.9 to 27.8° C. (24.6° C. in average) and the humidity was from 52 to 64% RH (57.3% RH in average). In a control plot, the same operation was carried out except that the essential oil solution was not sprayed on the filter paper. In this connection, the test was carried out three times.

The sprayed amount of essential oil solution in each test and the knockdown ratio (%), death rate and average death rate (%) calculated based on the following formulae are shown in Table 1.

Knockdown ratio (%)=knocked down numbers/the number of mites tested (50 individuals)×100

Death rate (%)=the number of deaths/the number of mites tested (50 individuals)×100

TABLE 1

| Essential oil solution | Test No. | Sprayed amount of essential oil solution (g) | Knockdown ratio (%) after 30 min | Knockdown ratio (%) after 24 hr | Death rate (%) | Average death rate (%) |
|---|---|---|---|---|---|---|
| Essential oil solution (A) | 1 | 0.463 | 100 | 96 | 96 | |
| (mint oil-eucalyptus oil solution) | 2 | 0.398 | 100 | 94 | 94 | |
| | 3 | 0.424 | 100 | 96 | 96 | 95.3 |
| Essential oil solution (B) | 1 | 0.412 | 100 | 94 | 94 | |
| (mint oil-rosemary oil solution) | 2 | 0.398 | 100 | 98 | 98 | |
| | 3 | 0.418 | 100 | 90 | 90 | 94.0 |
| Essential oil solution (C) | 1 | 0.440 | 100 | 94 | 94 | |
| (mint oil solution) | 2 | 0.431 | 100 | 100 | 100 | |
| | 3 | 0.436 | 100 | 90 | 90 | 94.7 |
| Control plot | 1 | — | 0 | 0 | 0 | |
| | 2 | — | 0 | 0 | 0 | |
| | 3 | — | 0 | 0 | 2 | 0.7 |

EXAMPLE 2

Sensory test of the essential oil solutions (A) to (C) prepared in Example 1 was carried out.

The sensory test was carried out by asking five testers (A, B, C, D and E) to decide ranking of smells of the essential oil solutions (A) to (C) in preferred order, and the results were evaluated by the total of the ranking (smaller total means superior result). The results are shown in Table 2.

TABLE 2

| Essential oil solution | A | B | C | D | E | Total ranking |
|---|---|---|---|---|---|---|
| Essential oil solution (A) (mint oil-eucalyptus oil solution) | 2 | 1 | 2 | 3 | 1 | 9 |
| Essential oil solution (B) (mint oil-rosemary oil solution) | 1 | 3 | 1 | 1 | 2 | 8 |
| Essential oil solution (C) (mint oil solution) | 3 | 2 | 3 | 2 | 3 | 13 |

EXAMPLE 3

An essential oil mixture was obtained by mixing eucalyptus oil and peppermint oil at a weight ratio of 1:23. Next, 12 parts by mass of this essential oil mixture was mixed with 88 parts by mass of 95% by volume ethanol aqueous solution to obtain an essential oil solution (D). When the miticide effect of this essential oil solution (D) was evaluated, similar effect of the essential oil solutions (A) to (C) was obtained. Also, as a result of the sensory test carried out by five testers, four testers answered that it smelled sweeter than the essential oil solution (C) (mint oil solution).

EXAMPLE 4

An essential oil mixture was obtained by mixing eucalyptus oil and peppermint oil at a weight ratio of 1:11. Next, 12 parts by mass of this essential oil mixture was mixed with 88 parts by mass of 95% by volume ethanol aqueous solution to obtain an essential oil solution (E). When the miticide effect of this essential oil solution (E) was evaluated, similar effect of the essential oil solutions (A) to (C) was obtained. Also, as a result of the sensory test carried out by five testers, four testers answered that it smelled sweeter than the essential oil solution (C) (mint oil solution).

EXAMPLE 5

An essential oil mixture was obtained by mixing rosemary oil and peppermint oil at a weight ratio of 1:11. Next, 12 parts by mass of this essential oil mixture was mixed with 88 parts by mass of 95% by volume ethanol aqueous solution to obtain an essential oil solution (F). When the miticide effect of this essential oil solution (F) was evaluated, similar effect of the essential oil solutions (A) to (C) was obtained. Also, as a result of the sensory test carried out by five testers, four testers answered that it smelled sweeter than the essential oil solution (C) (mint oil solution).

Though examples of the use of peppermint oil as a mint oil have been described in the foregoing, similar effect can also be obtained when a mint-distilled oil, a dementholized oil or spearmint oil is used instead of peppermint oil.

Since the essential oil mixture and miticide composition of the invention use natural essential oils as the active ingredients, they have high safety for human bodies and hardly give users unpleasant feeling when used until exerting the miticide effect. Accordingly, the essential oil mixture for miticide and miticide composition of the invention can be used suitably for exterminating mites inhabiting places such as mats, rugs, carpets, sofas, mattresses and bedclothes which contact directly with human bodies.

The term "mass", "by mass ratio", and "part(s) by mass" as used in this specification has the same meaning with "weight", "by weight ratio", and "part(s) by weight", respectively.

While the invention has been described in detail and with reference to specific embodiments thereof, it will be apparent to one skilled in the art that various changes and modifications can be made therein without departing from the scope thereof.

This application is based on Japanese patent application No. 2001-112185 filed Apr. 11, 2001, the entire contents thereof being hereby incorporated by reference.

What is claimed is:

1. An essential oil mixture for miticide, consisting essentially of eucalyptus oil or rosemary oil or a mixture thereof and at least one mint oil selected from the group consisting of peppermint oil, a distilled oil, a dementholized oil, and spearmint oil in amounts of eucalyptus oil or rosemary oil or a mixture thereof to mint oil within a range of from 1:4 to 1:99 by mass ratio and one or more solvents selected from the group consisting of alcohols and a mixed solution of these alcohols with water.

2. The essential oil mixture for miticide according to claim 1, wherein the mint oil is peppermint oil.

3. A miticide composition which comprises an essential oil mixture for miticide comprising eucalyptus oil or rosemary oil or a mixture thereof and at least one mint oil selected from the group consisting of peppermint oil, a distilled oil, a dementholized oil, and a spearmint oil in amounts of eucalyptus oil or rosemary oil or a mixture thereof to mint oil within a range of from 1:4 to 1:99 by mass ratio.

4. The miticide composition according to claim 3, wherein the mint oil is peppermint oil.

5. A miticide composition which comprises a solvent and an essential oil mixture for miticide dissolved in said solvent, said essential oil mixture for miticide comprising eucalyptus oil or rosemary oil or a mixture thereof and at least one mint oil selected from the group consisting of peppermint oil, a distilled oil, a dementholized oil, and a spearmint oil in amounts of eucalyptus oil or rosemary oil or a mixture thereof to mint oil within a range of from 1:4 to 1:99 by mass ratio.

6. The miticide composition according to claim 5, wherein a content of the essential oil mixture for miticide is within a range of from 3 to 20% by mass based on the total amount of the miticide composition.

7. The miticide composition according to claim 5, wherein the mint oil is peppermint oil.

8. A spray for miticide, which comprises a closed container having a spray nozzle and the miticide composition of any one of claims 3 to 7 packed therein.

9. The essential oil mixture for miticide according to claim 1, wherein the solvent is an alcohol selected from the group consisting of ethyl alcohol, isopropyl alcohol, ethylene glycol, glycerol, propylene glycol, dipropylene glycol and 1,3-butylene glycol, or a mixed solution of these alcohols with water.

* * * * *